(12) United States Patent
Weber et al.

(10) Patent No.: US 7,214,484 B2
(45) Date of Patent: May 8, 2007

(54) COMPOSITIONS AND METHODS FOR NUCLEIC ACID EXTRACTION FROM BIOLOGICAL SAMPLES

(75) Inventors: Scott A. Weber, St. Louis, MO (US); Derek K. Douglas, St. Louis, MO (US); Carol Kreader, St. Louis, MO (US)

(73) Assignee: Sigma-Aldrich Co., St. Louis, MO (US)

( * ) Notice: Subject to any disclaimer, the term of this patent is extended or adjusted under 35 U.S.C. 154(b) by 465 days.

(21) Appl. No.: 10/322,103

(22) Filed: Dec. 17, 2002

(65) Prior Publication Data

US 2004/0115658 A1 Jun. 17, 2004

(51) Int. Cl.
*C12P 19/34* (2006.01)
*C12N 1/08* (2006.01)
*C12Q 1/68* (2006.01)

(52) U.S. Cl. .......................................................... 435/6
(58) Field of Classification Search ...................... 435/6
See application file for complete search history.

(56) References Cited

U.S. PATENT DOCUMENTS

| 6,309,827 B1 | 10/2001 | Goldstein et al. | |
|---|---|---|---|
| 6,455,252 B1 * | 9/2002 | Wade et al. | 435/6 |
| 6,936,414 B2 * | 8/2005 | Gundling | 435/6 |

FOREIGN PATENT DOCUMENTS

| CN | 1370842 A | 9/2002 |
|---|---|---|
| WO | 00/40697 A1 | 7/2000 |

OTHER PUBLICATIONS

Stratagene, 1993 Catalog, p. 74.*
Goldenberger, et al., *PCR Methods and Applications*, 4:368-370, 1995.
Zimmermann, et al., *Comparative Medicine*, 50:314-316, 2000.
GenElute™ Mammalian Genomic DNA Miniprep kit, May 2002.
Drews, et al., *BioTechniques*, 17:866-867, 1994.
Chen, et al., *BioTechniques*, 8:32-33, 1990.
Ren, et al., *Contemp. Top. Lab. Anim. Sci.* (*US*), 40:27-30, 2001.
Thomson, et al., *BioTechniques*, 19:394-400, 2002.
McCarthy, et al., *BioTechniques*, 32:560-564, 2002.
Yokota, et al., *J. Clin. Lab. Anal.*, 14:97-100, 2000.
Guidet, *Nucleic Acids Res.*, 22:1772-1773, 1994.
Bajorath et al., "Long-Range Structural Changes in Porteinase K Triggered by Calcium Ion Removal," Nature, 1989, vol. 337, pp. 481-484.
Barrett et al., "Perspectives in Biochemistry and Biophysics," Arch. Biochem. and Biophys., 1995, vol. 318(2), pp. 247-250.
Baumforth et al., "The Polymerase Chain Reaction," J. Clin. Pathol.: Mol. Pathol., 1999, vol. 52(1), pp. 1-10.
Gelfand, H.G., "Taq DNA Polymerase," PCR Technology, H. A. Erlich, Ed., Stockton Press, N.Y., 1989. pp. 17-22.
Muller et al., "Crystal Structure of Calcium-Free Proteinase K at 1.5-Å Resolution," J. Biol. Chem., 1994, vol. 269(37), pp. 23108-23111.
Siezen et al., "Subtilases: The Superfamily of Subtilisin-Like Serine Proteases," Protein Science, 1997, vol. 6, pp. 501-523.
Steiner et al., "A Rapid One-Tube Genomic DNA Extraction Process for PCR and RAPD Analyses," Nucl. Acids Res., 1995, vol. 23(13), pp. 2569-2570.
International Search Report for PCT/US03/37657 dated Aug. 9, 2004.
Drews, R., et al., "Transgene Detection in Mouse Tail Digests," BioTechniques, 1994, vol. 17(5), pp. 866-867.
Supplementary European Search Report, EP 03 79 6447, dated Dec. 4, 2006, 3 pages.

* cited by examiner

*Primary Examiner*—Jon Weber
*Assistant Examiner*—Kailash C. Srivastava
(74) *Attorney, Agent, or Firm*—Senniger Powers; Brian K. Stierwalt; Jeffrey Wilson

(57) ABSTRACT

Methods and compositions for extracting nucleic acids from a biological sample are provided. The extraction compositions contain a protease enzyme such as proteinase K at alkaline pH with little or no surfactant present. Extraction can be efficiently performed in 60 minutes or less at room temperature for certain mammalian tissue samples and at elevated temperatures for certain plant tissues.

11 Claims, 6 Drawing Sheets

COMPOSITIONS AND METHODS FOR NUCLEIC ACID EXTRACTION FROM BIOLOGICAL SAMPLES

BACKGROUND OF THE INVENTION (1) Field of the Invention

This invention relates generally to methods and compositions for the extraction of nucleic acids from biological samples, and, more particularly, to methods and compositions for rapid extraction of nucleic acids from tissue samples using an alkaline solution containing proteinase K. The extraction solution is suitable for further processing of the extracted nucleic acid using PCR.

(2) Description of the Related Art

With the advent of modern molecular biology, the ability to study nucleic acids in biological samples has allowed many significant advances in biological and biochemical research. One method that has provided such advances has been the polymerase chain reaction (PCR) which allows the rapid amplification of target nucleic acid from as little starting material as a single molecule (for review see Baumforth et al, *J. Clin. Pathol. Mol. Pathol.* 52:1–10, 1999; Rapley et al, *Medical Laboratory Sciences* 49:119–128, 1992).

The application of PCR and other methods in molecular biology require the extraction of nucleic acid from biological samples and a number of approaches have been devised for performing such extraction. Various approaches have included treatment with a surface active agent such as sodium dodecyl sulfate and proteinase K to lyse cells and release the nucleic acid along with extraction using phenol and/or chloroform (see, for example, Sambrook et al., *Molecular Cloning A Laboratory Manual, Second Edition*, Cold Spring Harbor Laboratory Press, Cold Spring Harbor, N.Y., 1989).

In recent years, a number of approaches have been developed for rapid extraction of nucleic acids from biological samples. The methods not only provide an ease and convenience of tissue processing, they allow the processing of a high volume of samples (see for example, Steiner et al, *Nucleic Acids Research* 23:2569–2570, 1995). Nevertheless, efficient extraction of biological samples has not always been achieved.

Both animal and plant tissues have been studied and approaches for nucleic acid extraction have been developed for both. For mammalian tissue extraction, some studies have reported on the digestion of the tissue by incubation with proteinase K for hours at elevated temperatures (see for example, Goldenberger et al., *PCR Methods and Applications* 4: 368–370, 1995; Zimmermann et al., *Comparative Medicine* 50:314–316, 2000) Such methods can form the basis for kits, which are commercially available (see for example GenElute™ Mammalian Genomic DNA Miniprep kit available from Sigma-Aldrich, St. Louis Mo.).

Other studies have reported shorter incubation times, which are more applicable for use in high throughput assays. For example, U.S. Pat. No. 6,469,159 discloses an extraction method using a buffer, a non-ionic surfactant and heating at alkaline pH. Heating was to 70° C. to 100° C. for 5 minutes to 3 hours. This reference, however, did not disclose extraction at temperatures less than 70° C., which could have been more conveniently performed or the use of an extraction solution, which did not contain a surfactant.

Drews et al. reported on a 15 minute procedure for extraction of mouse tail sections at 55° C. The procedure used a Tris-HCl buffer at pH 8.0 and containing the ionic surfactant, sodium dodecyl sulfate (SDS), and Proteinase K (Drews et al., *BioTechniques* 17:866–867, 1994). Similarly, Chen et al. reported on a 30 min procedure for extracting mouse ear-punch tissues at 55° C. using a Tris-HCl buffer at pH 8.0, SDS and Proteinase K (Chen et al., *BioTechniques* 8:32–33, 1990). Although SDS is known to inhibit Taq polymerase in PCR reactions (e.g. see Gelfand, in *PCR Technology*, H. A. Erlich, Ed., Stockton Press, N.Y., 1989 pp. 17–22), these groups provided no suggestion that extraction could be carried out without surfactant. In addition, there was no suggestion in these references that extraction of the mouse tissues might have been carried out at room temperature, which would have been more convenient.

Ren et al, however, reported on the extraction of mouse ear-punch tissue using a detergent-free, proteinase K solution in sterile water at room temperature for 30 min (Ren et al., *Contemp. Top. Lab. Anim. Sci.* (*US*) 40:27–30, 2001). This group, however, did not use a Tris-HCl buffer and particularly noted the absence of strong bases and acids in their extraction solution.

Methods for rapid extraction of plant tissues have also been reported. Thomson et al. reported on the extraction of DNA from ground leaf, seeds and embryos using a Tris-HCl buffer at pH 9.5 and incubation at 95° for 5–60 min and at 65° for 10–60 min (Thomson et al, *BioTechniques* 19:394–400, 2002). McCarthy et al. reported on the extraction of DNA from ground transgenic wheat seeds at room temperature using an extraction buffer containing urea, SDS and EDTA. A 1:1 phenol:chloroform mixture was then added to the extraction buffer (*BioTechniques* 32:560–564, 2002). Steiner et al. reported on the extraction of lyophilized and ground leaf tissue at 90° for 20 min using an extraction buffer containing Tris-HCl at pH 8, sodium lauryl sarkosyl and polyvinylpolypyrrolidone. None of these groups reported on the use of a protease enzyme such as Proteinase K in the extraction buffer.

Guidet reported incorporating Proteinase K into the extraction buffer to extract DNA from lyophilized and crushed leaf samples (Guidet, *Nucleic Acids Res.* 21:4153–4154, 1994). The buffer contained Tris-HCl at pH 8, EDTA, sodium lauryl sarkosyl and Proteinase K and the extraction was at 50° C. for 1 hour. The Proteinase K, however, may not have significantly contributed to the extraction since the EDTA, which is known to be a $Ca^{2+}$ chelator, was present at a concentration of 450 mM. This is because Proteinase K is $Ca^{2+}$-dependent in that the enzyme is unstable at the high temperatures used by Guidet as well as exhibiting a decrease in enzyme activity in the absence of $Ca^{2+}$ (Bajorath et al., *Nature* 337:481–484, 1989; Muller et al, *J. Biol. Chem.* 269:23108–23111; Kolvenbach et al., *Int. J. Pept. Protein Res* 36:387–391, 1990). Moreover, the detergent, sodium lauryl sarkosyl is present which may affect subsequent PCR amplification (Gelfand, supra, 1989).

Thus, in view of the deficiencies of earlier methods and compositions, there remains a continuing need for improved methods and compositions for extracting nucleic acids from plant and animal samples.

BRIEF SUMMARY OF THE INVENTION

Accordingly, the inventors herein have succeeded in discovering that an extraction composition which comprises a protease enzyme and which contains a buffering component to buffer the composition to an alkaline pH of 7.5 or greater, can be used to efficiently extract nucleic acids from animal or plant samples. One protease enzyme suitable for use in the present invention is Proteinase K. By extraction of nucleic acids from a sample it is meant that the release of nucleic acid from tissue components is effected so that subsequent procedures such as PCR can be performed. In the subsequent PCR procedures, the threshold cycle value ($C_t$) is detectable over background. The $C_t$ value will depend upon instrumentation and detection system used and can be readily ascertained by the skilled artisan. Typical $C_t$ values are less than or equal to about 20, less than or equal to about 35 or less than or equal to about 50 or less than or equal to any value therebetween. Nucleic acids are, thus, extracted in such a manner that the nucleic acids can be subsequently amplified by PCR. It is possible that PCR inhibitors which would prevent amplification could be present in the extraction solution, whether obtained as part of the extraction process from the biological sample or from some other source. The presence of PCR inhibitors in the extraction solution would result in little or no amplification of nucleic acids and this would be deemed to constitute absence of effective extraction from the sample. Because surfactants can sometimes interfere with subsequent PCR amplification, the extraction composition, in certain embodiments, preferably, does not contain surfactants. The term "surfactant" as used herein is intended mean a surface active substance, which is used herein interchangeably with the term "surfactant". Surfactants include anionic surfactants, cationic surfactants, non-ionic surfactants and zwitterionic surfactants. Although surfactants are not included in the extraction compositions of certain embodiments, surfactants may, nevertheless, be included in the extraction compositions of certain other embodiments.

In addition, because an absence of $Ca^{2+}$ can, in some instances, decrease protease activity either directly or indirectly (Id., Muller et al., supra, 1994; Bajorath et al, supra, 1989), the extraction composition, preferably, does not contain a high concentration of a $Ca^{2+}$-chelator such as EDTA. Preferably, if present at all, the $Ca^{2+}$-chelator is at a concentration of not more than about 100 mM, not more than about 50 mM, not more than about 25 mM or not more than about 10 mM in the extraction composition.

Samples can be from any of a wide variety of biological sources including the non-limiting examples of species of animals such as, mammals including humans, fish, birds, insects such as *drosophila*, nematodes such as *C. elegans* and the like; plants including moss, ferns, trees, bushes, flowering plants and the like; fungi including mushrooms, molds, yeast and the like; protista including amea, paramecium, algae, seaweed, diatoms and the like; or monera including species of bacteria or cyanobacteria. Samples of tissues are considered to be distinct from samples of isolated cells such as, for example, blood cells, cells from tissue culture preparations or cells isolated by any process from a tissue or biopsy sample. The term tissue as used herein includes plant seeds and seed tissues. Generally, it is more difficult to extract nucleic acids from tissues than to extract nucleic acids from cells although this is not always the case.

Samples such as tissues or cells from a human or other mammal can be extracted at room temperature upon incubation for not more than about 30 minutes, and in certain aspects of the invention, not more than 20 minutes, and in other aspects, not more than about 10 minutes or not more than about 5 minutes. A preferred incubation time is about 10 minutes. Reference to room temperature or ambient temperature which may be used interchangeably herein, is intended to mean a laboratory temperature in which humans can perform tissue extractions, in absence of applied heat to the extraction mixture. Room temperature is typically about 20° C. or less, about 22° C. or less, up to about 25° C. or less, or, in some instances, up to even higher temperatures as would be readily understood by the skilled artisan.

Samples from plant tissues, such as portions of leaf or seed can be extracted at room temperature or at an increased temperature above room temperature. Extraction temperatures for plant tissues are sufficiently high to facilitate extraction, but not so high as to cause denaturation of the protease enzyme. In certain embodiments, extraction of plant tissue is carried out at an increased temperature of at least about 37° C., at least about 45° C., at least about 50° C., at least about 55° C., or at least about 60° C. or higher, depending upon the heat stability of the particular protease enzyme.

Thus in certain aspects, the present invention is directed to a method for extracting nucleic acid from a biological sample. The method comprises incubating the sample in an extraction composition, which is buffered to an alkaline pH of about 7.5 or greater. The extraction composition comprises a protease enzyme and does not contain a surface active agent. Incubation time for extraction of nucleic acids from samples are, preferably for sufficient time to release the nucleic acid, but not more than about 60 minutes. Incubation time, i.e. extraction time can be, in certain instances, about 5 minutes, about 10 minutes, about 20 minutes, about 30 minutes or about 45 minutes.

In another aspect, the present invention provides a method for extracting nucleic acid from a biological sample obtained from a mammal. The method comprises incubating the sample at room temperature in an extraction composition, which is buffered to a pH of 7.5 or greater for an incubation time of not more than 30 minutes.

In still another aspect of the present invention, there is provided a method for extracting nucleic acid from a biological sample obtained from a plant. The method comprises incubating the sample at room temperature or at an increased temperature in a range of temperatures of from a minimum of at least about 37° C. or at least about 45° C. up to a maximum of not more than about 60° C. in an extraction composition. The extraction composition is buffered to a pH of 7.5 or greater. Incubation is for a period of time of not more than 30 minutes.

The present invention also includes compositions and kits for extracting nucleic acid from a biological sample. The compositions and kits are comprised of an extraction composition, which comprises a protease enzyme and a buffering agent, which maintains the pH of the composition at 7.5 or greater. In certain instances a $Ca^{2+}$-chelator such as EDTA can be present and, if present, it is at a concentration of not more than 100 mM. The extraction composition of the kits can be a single composition or the individual components of the extraction composition can be maintained separately for mixing prior to use. Thus the components of the nucleic acid extraction composition in the kits of the present invention, can be packaged separately or in one or more mixtures of any combination the components. Each of the separate components or one or more mixtures are in a different container and a single container can contain the overall kit. Preferably, the extraction compositions of the kits and compositions of the present invention do not include a surface active agent.

DETAILED DESCRIPTION OF THE INVENTION

Figure 1:
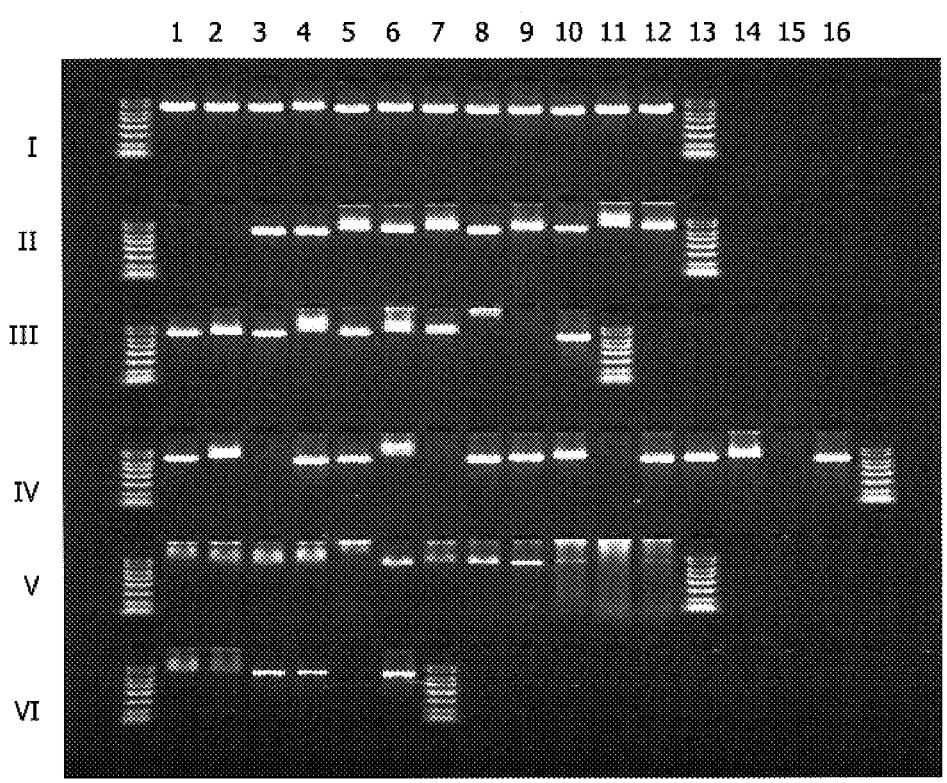
FIG. 1 illustrates in duplicate samples, agarose gel electrophoresis of PCR amplification products from extracted tissues as follows: Row I shows the products of duplicate samples of mouse ear punch tissues using the extraction method herein with incubation at room temperature for 10 minutes (lanes 1 and 2), 20 minutes (lanes 3 and 4) or for 30 minutes (lanes 5 and 6) or incubation at 55° C. is for 10 minutes (lanes 7 and 8), 20 minutes (lanes 9 and 10) and 30 minutes (lanes 11 and 12). Row II shows amplified DNA extracted from mouse ear punches illustrating the effect of the absence (lanes 1 and 2) of heating to 95° C. for 3 minutes following a 10 minute, room-temperature extraction; the lack of deleterious effect of omitting addition of the Neutralization Solution B (lanes 3 and 4) and the comparative effect of amplification of DNA obtained from mouse tails (lanes 5–12). Row III shows the effect of extraction of mouse tail at a pH adjusted to pH 10.5 (lanes 1 and 2), adjusted to pH 9.5 (lanes 3 and 4), adjusted to pH 8.5 (lanes 5 and 6), adjusted to pH 7.5 (lanes 7 and 8) and negative and positive controls (lanes 9 and 10). Row IV shows the lack of effect of varying the KCl concentration on extraction efficiency at 200 mM KCl (lanes 1 and 2), at 100 mM KCl (lanes 5 and 6), at 50 mM KCl (lanes 9 and 10) or at 0 mM KCl (lanes 13 and 14) with negative controls shown in lanes 3, 7, 11 and 15 and positive controls shown in lanes 4, 8, 12 and 16. Row V shows the PCR amplification products from extraction of mouse ear punch tissue using the methods of Ren et al. (Ren et al., *Contemp. Top. Lab. Anim. Sci.* (*US*) 40:27–30, 2001) following incubation at room temperature for 10 minutes (lanes 1 and 2), 20 minutes (lanes 3 and 4) or 30 minutes (lanes 5 and 6) and following incubation at 55° C. for 10 minutes (lanes 7 and 8), 20 minutes (lanes 9 and 10) or 30 minutes (lanes 11 and 12). Row VI shows the PCR amplification products from extraction of mouse ear punch tissue using a modification of the method of Ren et al. in which Neutralization Solution B was added at the end of extraction (lanes 1 and 2) and amplification by the method of Chen et al. (Chen et al., *BioTechniques* 8:32–33, 1990) following incubation at 55° C. for 30 minutes (lanes 3 and 4) with negative and positive control (lanes 5 and 6).

In accordance with the present invention, it has been discovered that nucleic acids can be efficiently extracted from biological samples using an extraction composition which contains a protease enzyme and which is buffered to an alkaline pH of 7.5 or greater.

The protease enzyme serves to produce at least a partial tissue break down such that nucleic acids are released. As such, any substance, which serves the same function, can be used in the extraction composition. The terms proteases, proteinases and peptidases are used interchangeably herein and refer to the group of enzymes that catalyze the hydrolysis of covalent peptidic bonds. Protease enzymes are well known in the art and serine proteases are one group of proteases. Six clans of serine proteases have been identified, the two largest of which are the chymotrypsin-like and the subtilisin-like clans (Rawlings et al. *Methods Enzymol* 244: 19–61, 1994; Barrett et al, *Arch. Biochem. Biophys.* 318: 247–250, 1995). A large number of subtilases are known (Siezen et al, *Protein Science* 6:501–523, 1997; Siezen et al., *Protein Engineering* 4:719–737, 1991). Some of the subtilases which have been extensively studied include those obtained from various species of Bacillus including subtilisin DY, subtilisin Carlsberg, subtilisin BPN' (also called nagarse), mesentericopeptidase as well as proteinase K which is obtained from *Tritirachium album* Limber and thermitase which is obtained from *Thermoactinomyces vulgaris*. In certain embodiments of the present invention, proteinase K is preferred as a protease enzyme. Other protease enzymes, however, can also be used in certain embodiments, such as, for example, nagarse (for characterization of nagarse see Masaharu et al, *J. Clin. Lab. Anal.* 14:97–100, 2000). The protease enzyme can thus be any of a number of proteases that produce at least a partial break down of the biological sample such that nucleic acids are released within a short period of, for example about 60 minutes or less.

Proteinase K is commercially available as a lyophilized powder or in aqueous solutions or suspension (Sigma-Aldrich, St. Louis, Mo.). Activity is generally referenced in Units, which are defined as the activity necessary to release folin-positive amino acids and peptides corresponding to 1 µM of tyrosine per minute using hemoglobin as substrate in 30 mM Tris-HCl, pH 7.5 at 37° C. The typical activity of proteinase K preparations is about 30 Units/mg. The concentrations of proteinase K in the extraction composition is preferably at least about 25 Units/ml or greater, at least about 50 Units/ml or greater or at least about 100 Units/ml or greater. Maximal concentrations can be up to about 200 Units/ml, up to about 400 Units/ml, or up to about 800 Units/ml, the upper limit of concentration being effected by solubility of the enzyme as well as the ability to sufficiently denature the enzyme at the end of extraction so that there will be no decrease in DNA polymerase activity during subsequent PCR amplification of the extracted nucleic acid.

The extraction composition of the present invention is typically an aqueous solution, however, in certain embodiments, the extraction composition can be in the form of an aqueous dispersion, suspension, emulsion or the like. The aqueous portion of the extraction composition is at an alkaline pH of about 7.5 or greater. Preferably, the extraction composition pH is at least about 8.0 or greater, at least about 8.5 or greater, at least about 9.0 or greater and in a range of from about 7.5 to about 10, in a range of from about 8.0 to about 9.0, or in a range of from about 8.0 to about 8.5.

Any of a number of buffering agents can be used in the extraction composition the selection and use of which can be readily performed by the skilled artisan (see for example Beynon and Esterby, *Buffer Solutions: The basics*, BIOS Scientific Publishers, Oxford, 1996). Preferably, the buffer is prepared from a substance have a pKa value from one unit less than to one unit greater than the desired pH. Thus, for example, a pH 8.0 buffer can be prepared using a substance having a pKa from about 7.0 to 9.0. Such buffer substances include, for example, AMPD (2-Amino-2-methyl-1,3-propanediol), bicarbonate (Sodium hydrogen carbonate), Bicine (N,N-Bis-(2-hydroxyethyl)-glycine), Bis-Tris-Propane (1,3-Bis-[tris-(hydroxymethyl)-methylamino]-propane),), DIPSO(N,N-Bis-(2-hydroxyethyl)-3-amino-2-hydroxypropanesulfonic acid), glycylglycine HEPES (4-(2-Hydroxyethyl)-piperazine-1-ethanesulfonic aicd), HEPPS (4-(2-Hydroxyethyl)-piperazine-1-propanesulfonic acid), HEPPSO (4-(2-Hydroxyethyl)-piperazine-1(2-hydroxy)-propane-sulfonic acid), phosphate, POPSO (Piperazine-1,4-bis-(2-hydroxypropanesulfonic acid)), TAPS (N-[Tris-(hydroxymethyl)-methyl]-3-aminopropanesulfonic acid), TAPSO (N-[Tris-(hydroxymethyl)-methyl]-3-amino-2-hydroxypropanesulfonic acid) TES (N-[Tris-(hydroxymethyl)-methyl]-2-aminoethanesulfonic acid), Tricine (N-[Tris-(hydroxymethyl)-methyl]-glycine), Tris (Tris-(hydroxymethyl)-aminomethane) and triethanolamine. Preferred as a buffer component is Tris-HCl, which is typically prepared by dissolving Tris base in water and adding HCl to achieve the desired pH. Buffers from other substances as those identified above, can be readily prepared by the skilled artisan by methods well known in the art.

As noted above, surfactants are preferably, not present in the extraction compositions of certain embodiments. Both ionic and non-ionic surfactants are absent from such embodiments. By a surfactant not being present of the composition lacking a surfactant or the surfactant being absent from the extraction composition, it is meant that any concentration of the surfactant is negligible as would be readily understood by the skilled artisan. Such negligible amounts present are considered to be less than about 0.5% (w/w), preferably, less than about 0.2% (w/w), preferably, less than about 0.1% (w/w).

$Ca^{2+}$ chelators are also, preferably, not present or at low concentrations in the extraction compositions of certain embodiments of the present invention. Thus, the $Ca^{2+}$ chelator, EDTA, if present in the extraction composition, is at a concentration of about 100 mM or less, preferably at a concentration of about 50 mM or less, preferably at a concentration of about 20 mM or less, preferably at a concentration of about 10 mM or less.

The extraction composition can be in two or more compositions which are mixed together to form the extraction composition. In one embodiment, the components can be in two solutions, an extraction solution and a sample preparation solution. The extraction solution can contain a buffer component, for example Tris-HCl. The Tris-HCl can be at a concentration of from about 10 mM to about 1000 mM, preferably, from about 20 mM to about 300 mM, preferably, from about 50 mM to about 200 mM and, preferably, about 100 mM. Along with the Tris-HCl, the extraction solution can contain a salt such as, for example KCl at a concentration of from about 0.1 to about 0.4 mM, preferably 0.2 to about 0.3 mM, and preferably about 0.25 mM. EDTA can also be present in the solution, for example at a concentration of from about 1 to about 40 mM, preferably, from about 5 to about 20 mM and preferably about 10 mM.

A sample preparation solution can contain the protease enzyme, such as, for example, proteinase K at a concentration of from about 100 to about 1000 Units/ml, preferably from about 200 to about 800 Units/ml, and preferably about 600 Units/ml. The second solution can also contain a buffer component such as, for example Tris-HCl, a water soluble calcium compound such as, for example calcium acetate or calcium chloride, and stabilizers and/or solubilizers for the proteinase K, such as, for example, glycerol. The extraction solution and sample preparation solution are contacted with the biological sample and the mixture incubated.

Incubation is, preferably, for about 60 minutes or less, preferably, about 45 minutes, preferably, about 30 minutes, preferably about 20 minutes, preferably about 10 minutes, preferably about 5 minutes or less. Typically, incubation is for about 10 minutes.

The temperature for incubation will depend upon the biological sample being extracted. For example, for mammalian tissues, extraction is preferably, at room temperature, preferably no more than about 25° C., preferably no more than about 22° C. and, in particular, about 20° C., about 22° C., or about 25° C. For other biological samples, for example, plant tissues, extraction temperatures can be from about 37° C. to about 60° C., preferably from about 50° C. to about 55° C. The incubation temperature is maintained below the temperature at which the protease enzyme becomes denatured, for example below about 65° C. for proteinase K.

Nucleic acids can be extracted from any of a wide variety of biological samples using the extraction composition of the present invention. As discussed above, the samples can be obtained from animals such as, mammals including humans, fish, birds, insects such as *drosophila*, nematodes such as *C. elegans* and the like; plants including moss, ferns, trees, bushes, flowering plants and the like; fungi including mushrooms, molds, yeast and the like; protista including amoeba, paramecium, algae, seaweed, diatoms and the like; or monera including species of bacteria or cyanobacteria. Biological samples from plants can include leaf samples, seed samples or samples from other plant tissues. Samples from animals can include tissue and cell samples from mammals and, in particular, from humans. Mammalian tissue samples can be obtained by any method known in the art such as for example from mouse ear punch or from mouse tail portion. The samples can be prepared such as by lyophilization or drying by other methods. In certain embodiments such as, for example, for the extraction of certain plant tissues, samples may be minced or ground to facilitate the extraction process.

One particular method can involve pipetting the extraction solution and the sample preparation solution into a microcentrifuge tube or well of a multiwell plate. For mammalian tissue extraction about 100 µl of extraction solution and about 25 µl of sample preparation solution are added and then mixed. A mammalian tissue sample of about 2 to 10 mg of tissue is placed in the solution. The sample is then incubated at room temperature for 10 minutes. After the incubation period, the sample and solution are heated to 95° C. for about 3 minutes. This stops the extraction process and denatures the proteinase K, which will allow for subsequent PCR amplification of the extracted DNA.

Optionally, a neutralization solution, containing albumin can then be added to the mixture. The extracted DNA can then be used in further methods as are known in the art such as, for example, in PCR, sequencing and the like.

Kits of the present invention can contain components of the extraction composition packaged separately or in one or more mixtures of any combination to components. Thus, a kit can contain, for example, an extraction solution and a sample preparation solution each packaged in a separate container. Optionally, other components can be included in the kit such as, for example, a neutralization solution. In addition, the kits can also contain components for performing PCR amplifications such as are commercially available in kit form (Sigma-Aldrich, St. Louis, Mo.).

Illustrative examples are described below. Unless otherwise indicated, all materials used in the examples were obtained from Sigma-Aldrich Corporation, St. Louis, Mo.

EXAMPLE 1

This example illustrates the extraction of DNA from mammalian tissue samples, *Drosophila* samples, *C. elegans* samples and from plant seed samples.

The extraction method uses an extraction solution, a tissue preparation solution and a neutralization solution. The Extraction Solution (referenced herein as E7526) contains 0.25 M KCl, 0.01 M EDTA and 0.1 M Tris-HCl, at a pH of 9.5. The Sample Preparation Solution contains Proteamase K from *Tritirachium Album* Libium in an aqueous solution (~800 Units/mL) containing 40% glycerol, 1 mM calcium acetate and 10 mM Tris-HCl at pH 7.5. The Neutralization Solution B contains 3% bovine albumin and 10 ppm Kathon.

The following procedures are carried out for extraction of DNA from mammalian, *drosophila* or *C. elegans* samples at room temperature and from seed samples at 55° C.

A. DNA Extraction from Mouse Tails, Animal Tissues, Hair, Saliva, *Drosophila* or *C. elegans*.

100 µl of Extraction Solution is placed into a microcentrifuge tube or well of a multiwell plate. 25 µl of Sample Preparation Solution are added to the tube or well and the two solutions are mixed by pipetting up and down. If several extractions are to be performed, sufficient volumes of Extraction and Sample Preparation Solutions may be pre-mixed in a ratio of 4:1 up to 2 hours before use.

Sample preparation and addition to the prepared solution is as follows:

(i) For Fresh or Frozen Mouse Tails: Scissors and forceps are rinsed in 70% ethanol prior to use and between different samples. A 0.5 to 1 cm piece of mouse tail tip is placed into the solution, cut end down. Thorough mixing is achieved by vortexing or pipetting. Care is taken to ensure that the mouse tail is in solution. For fresh mouse tails, extractions are within 30 minutes of the tail being snipped.

(ii) For Animal tissues: Scissors or scalpel and forceps are rinsed in 70% ethanol prior to use and between different samples. A 2 to 10 mg piece of tissue is placed into the solution. Thorough mixing is achieved by vortexing or pipetting. Care is taken to ensure that the tissue is in the solution.

(iii) For Hair Shafts: Scissors and forceps are rinsed in 70% ethanol prior to use and between different samples. Excess hair shaft is trimmed off leaving the root and the sample is placed into solution, root end down.

(iv) For Saliva: 10 µl of saliva are pipetted into the solution. Thorough mixing is achieved by vortexing or pipetting.

(v) For Saliva Dried on Card: 50 µl of saliva are pipetted onto collection card and card is allowed to dry. Punch is rinsed in 70% ethanol prior to use and between different samples. Disk (preferably ⅛ inch) is punched out of card from area with dried saliva sample. Disk is placed into the solution. Tube or plate is tapped on hard surface to insure disk is in solution for incubation period.

(vi) For *Drosophila:* 1 to 10 anesthetized flies are crushed into the solution. Thorough mixing is achieved by vortexing or pipetting. Care is taken to ensure that the fly material is in the solution.

(vii) For *C. elegans:* 1 to 10 worms are added to the solution. Thorough mixing is achieved by vortexing or pipetting. Care is taken to ensure that the *C. elegans* material is in the solution.

Following addition of the sample to solution the sample is incubated at room temperature for 10 minutes to extract the DNA. For less than 10 *Drosophila* or *C. elegans*, release of DNA may be enhanced by performing this incubation at 55° C.

Following the incubation for extraction, the sample is heated to 95° C. for 3 minutes to denature the proteinase K.

100 µl of Neutralization Solution B is then added to the sample and mixing is achieved by vortexing.

The neutralized tissue extract is used immediately in PCR or stored at 4° C. for PCR at a later time. Extracts may be stored at 4° C. for up to 6 months; however, it is desirable to remove the undigested tissue before long term storage.

B. DNA Extraction for Buccal Swabs.

First, buccal cells are collected on swab and allowed to dry. Drying time is approximately 10 to 15 minutes.

200 µl of Extraction Solution is pipetted into a microcentrifuge tube. 25 µl of Sample Preparation Solution is added to the tube and pipetted up and down to mix. If several extractions are to be performed, sufficient volumes of Extraction and Sample Preparation Solution may be pre-mixed in a ratio of 8:1 up to 2 hours before use.

The dried buccal swab is placed into the solution and incubated at room temperature for 1 minute.

The swab is twirled in solution 10 times and then excess solution is removed from the swab into the tube by twirling the swab firmly against the side of the tube. The swab is then discarded. The tube is then closed and vortexed briefly.

The sample is then incubated at room temperature for 10 minutes to extract DNA.

Following the incubation for extraction, the sample is heated to 95° C. for 3 minutes to denature the proteinase K.

200 µl of Neutralization Solution B is then added to the sample and mixing is achieved by vortexing.

The neutralized tissue extract is used immediately in PCR or stored at 4° C. for PCR at a later time. Extracts may be stored at 4° C. for up to 6 months without notable loss in most cases.

C. DNA Extraction from Plant Seeds:

First, seed is ground by hand using plastic pestle or by use of a beadmill (2000 Geno/Grinder, Spex Certiprep, Inc., Metuchen, N.J.) in a volume of water of from 100 to 800 μl depending upon the volume of seed used. If grinding is to be done manually with a plastic pestle, the seed is soaked in water at 55° C. for 1 hour before grinding.

45 μl of Extraction Solution and 5 μl of Sample Preparation Solution are mixed together in a microcentrifuge tube or well of a multiwell plate. 5 μl of ground seed is placed into the mixture.

The mixture is then heated at 55° C. for 10 minutes to extract DNA.

The Extract is then heated at 95° C. for 3 minutes to denature the proteinase K.

50 μl of Neutralization Solution B is then added to the extract and the solutions are then mixed.

The neutralized seed extract is used immediately in PCR or stored at 4° C. for PCR at a later time. Extracts may be stored at 4° C. for up to 6 months without notable loss in most cases.

PCR can be directly performed on sample extracts obtained from the procedures above using Extract-N-Amp PCR Ready Mix or REDExtract-N-Amp PCR Ready Mix (Sigma-Aldrich, St. Louis, Mo.).

EXAMPLE 2

This example illustrates the extraction of DNA by the present method using tissues from mouse car punches and tail snips and compares extraction with earlier methods (Chen et al., 1990, supra; Ren et al., 2001, supra).

All materials were obtained from Sigma-Aldrich (St. Louis, Mo.) unless otherwise noted. PCR primers were obtained from SigmaGenosys (The Woodlands, Tex.).

Tissue samples obtained were mouse ear punches (⅛ inch disc) and mouse tails (0.5 cm tail tip and next 0.5 cm section up from that tip). The tail pieces were either fresh or frozen from a previous tissue collection which had been stored at −20° C. Each extraction was setup by placing 1 mouse ear punch or mouse tail into a 1.5 ml microcentrifuge tube. Extraction using the present method was performed as described in Example 1. Comparative extractions were performed using the methods of Chen et al. (1990, supra) and Ren et al. (2001, supra).

Two tubes were prepared for the extractions of each condition. In the set of tubes using the instant method, 100 μl of Extraction Solution and 25 μl Sample Preparation Solution were pipetted and mixed together in each tube, which already contained either an mouse ear punch or mouse tail. For samples using the procedures of earlier methods, the methods outlined by Ren et al. in Table 1 of that reference were used (see Ren et al, 2001, supra). Briefly, for the Chen et al. method a solution of 20 μl of 50 mM Tris-HCl at pH 8.0, 20 mM NaCl, 1 mM EDTA, 1% SDS and 1 μg/μl proteinase K was used and for the Ren et al. method, 5 μl of proteinase K solution (3 μg/μl) in sterile water was used. The Ren et al. mixture was incubated at room temperature or 55° C. for 10, 20 & 30 minutes to extract the DNA. The Chen et al. method was performed as described earlier (Chen et al., 1990, supra).

Following incubation to extract the DNA, 100 μl of Neutralization Solution B was added. The extractions were then vortexed to ensure thorough mixing of reagents.

PCR Amplifications: For standard PCR in 8 tube strips, 10 μl of REDExtract-N-amp PCR™ Ready mix (Sigma-Aldrich, St. Louis, Mo.) for Extract-N-Amp extracts or 12.5 μl of JumpStart REDTaq ReadyMix PCR Reaction Mix (Sigma-Aldrich, St. Louis, Mo.) for Ren et al. and Chen et al. methods, both forward and reverse primers at 0.4 μM., and aliquots of the extracts, 4 μl of the extract using the present method or 1 μl of the extract using the Chen et al. or Ren et al. methods were combined in a final volume of 20 μl. PCR Primers for mouse ear punches & mouse tails produced an 1181 bp amplicon from the Mouse Interleukin One Beta (IL-1β) gene (5'-TCTGGGGTTGATGTAGGA-3' [SEQ ID NO:1] and 5'-GGGCTGGAAAAATGGTC-3' [SEQ ID NO:2]). Reactions were assembled at room temperature and placed in a GeneAmp PCR System 9700 (Perkin Elmer/Applied Biosystems, Foster City, Calif.). PCR conditions for mouse ear punch & mouse tail reactions were: 94° C. for 3 min, then 35 cycles of 94° C. for 45 sec, 58° C. for 60 sec, 72° C. for 120 sec, then 72° C. 7 min.

The completed reactions were analyzed by gel electrophoresis (5 μl/PCR reaction) on a 1×TBE 2% Seakem LE Plus 10×15 Latitude Precast agarose gel with 0.5 μg/ml Ethidium Bromide added from Biowhittaker Molecular Applications (Rockland, Me.) (cat. No. 57266-lot No. LT0826). The marker used on the gel was P9577 PCR Marker (Sigma-Aldrich, St. Louis, Mo.).

For quantitative PCR, which was done on an ABI PRISM™ 7700 Sequence Detection System (Perkin Elmer/Applied Biosystems, Foster City, Calif.), a 96 well plate was prepared using 10 μl of REDExtract-N-AMP™ PCR Ready mix (R4775) for Extract-N-Amp extracts or 12.5 μl of JumpStart REDTaq ReadyMix PCR Reaction Mix (P0982) for earlier methods, both forward and reverse primers for IL-1β at 0.4 μM, SYBR® Green I dye (40 ppm final) (Sigma-Aldrich), 0.6 μl of Reference Dye for Quantitative PCR 100X (Sigma-Aldrich), and aliquots of the extract, 4 μl of the extract using the present method or 11 μl of the extract using the earlier methods were combined in a final volume of 20 μl. PCR Primers for mouse ear punches & mouse tails produced an 1181 bp amplicon from the Mouse Interleukin One Beta (IL-1β) gene (5'-TCTGGGGTTGATGTAGGA-3' (SEQ ID NO:1) and 5'-GGGCTGGAAAAATGGTC-3') (SEQ ID NO:2). Reactions were assembled at room temperature in a laminar flow hood. PCR conditions for mouse ear punch & mouse tail reactions: 94° C. for 3 min, then 40 cycles of 94° C. for 30 sec, 58° C. for 30 sec, 72° C. for 90 sec.

Results are shown in FIG. 1. Duplicate samples were run side by side. Row I shows the results of extraction at room temperature for 10 minutes (lanes 1 and 2), 20 minutes (lanes 3 and 4) and for 30 minutes (lanes 5 and 6). Extraction at 55° C. is shown for 10 minutes (lanes 7 and 8), 20 minutes (lanes 9 and 10) and 30 minutes (lanes 11 and 12). As shown in the figure, a robust extraction of DNA was achieved with the present method under all conditions tested.

Row II illustrates the effect of the effect of not heating to 95° C. for 3 minutes by the lack of PCR amplification product (lanes 1 and 2).

Row II lanes 3 and 4 show PCR amplification product in absence of addition of the Neutralization Solution B.

Row II lanes 5–12 show PCR amplification product from fresh mouse tails illustrating a robust DNA extraction for this tissue as well.

Row V shows the results using the method of Ren et al. and Row VI shows the results using the method of Chen et al. As shown in Row V, the method of Ren et al. produced very little PCR amplification product following incubation at room temperature for 10 minutes (lanes 1 and 2) and 20 minutes (lanes 3 and 4) suggesting that very little DNA was extracted from the sample. Some possible extraction after 30 minutes incubation was suggested from the corresponding amplification product (lanes 5 and 6) in at least one of the duplicate runs. No more than slight improvement in the extraction of DNA was suggested from the amplification product produced following incubation at 55° C. for 10 minutes (lanes 7 and 8), 20 minutes (lanes 9 and 10) or 30 minutes (lanes 11 and 12).

The extraction method of Chen et al. at 55° C. produced a modest amount amplification product following incubation for 30 minutes (lanes 3 and 4). Lanes 1 and 2 show the results of extraction using a modification of the method of Ren et. al. in which Neutralization Solution B is added to the preparation.

Thus, the present method showed substantially greater extraction of DNA following incubation at room temperature for 10 minutes than was apparent with either the method of Chen et al. or the method of Ren et al. even upon incubation at 55° C. by the earlier methods.

EXAMPLE 3

This example illustrates the effect of pH and KCl concentration on extraction of DNA from tissue samples.

Frozen mouse tail cuttings were extracted and amplified as described in Example 2. Results are shown in FIG. 1, Rows III and IV.

PCR amplification following extraction at pH adjusted to pH 10.5 (lanes 1 and 2), adjusted to pH 9.5 (lanes 3 and 4), adjusted to pH 8.5 (lanes 5 and 6) and adjusted to pH 7.5 (lanes 7 and 8) with negative and positive controls in lanes 9 and 10. As can be seen in the figure, little difference in the extraction efficiency was seen from pH 8.5 to pH 10.5. At pH 7.5 one of the two preparations did not show PCR amplification product which suggests that extraction efficiency might begin to decrease as pH decreases to 7.5 and below.

KCl concentration did not show any effect on extraction efficiency at 200 mM KCl (lanes 1 and 2), at 100 mM KCl (lanes 5 and 6), at 50 mM KCl (lanes 9 and 10) or at 0 mM KCl (lanes 13 and 14). Lanes 3, 7, 11 and 15 and 4, 8, 12 and 16 are negative and positive controls, respectively.

EXAMPLE 4

This example illustrates the extraction of seeds in absence and presence of proteinase K.

The effect of the absence and presence of proteinase K on extraction efficiency was tested using Soybean, Sorghum and Arabidopsis seeds.

All materials were obtained from Sigma-Aldrich (St. Louis, Mo.) unless otherwise noted. All PCR primers were obtained from SigmaGenosys (The Woodlands, Tex.). The primers used were as follows:

```
Soybean 0513 bp:
Forward-5'-TTG GGA ACC TCT ACA TTC-3'   (SEQ ID NO:3)
Reverse-5'-CGG GCA GAA ACT AAA TC-3'    (SEQ ID NO:4)

Sorghum 0503 bp:
Forward-5'-ATT GGC GAT GGC AAG T-3'     (SEQ ID NO:5)
Reverse-5'-GAA TCT GCT GGG GTT CAG-3'   (SEQ ID NO:6)

Arabidopsis 2110 bp:
Forward-5'-ACT CTA CCT CGC CAC CAT-3'   (SEQ ID NO:7)
Reverse-5'-GCC CAC TCT GCT TCA AAC-3'   (SEQ ID NO:8)
```

Seeds were placed into wells of a 96 square well block. 1 seed was placed into each of two separate wells for Soybean and Sorghum. Around 50 Arabidopsis seeds were placed into each of two separate wells. A single Stainless Steel grinding ball was placed into each seed containing well. 800 µl of water was pipetted into the wells containing soybean seeds. 200 µl of water was pipetted into the wells containing sorghum seeds. 100 µl of water was pipetted into the wells containing arabidopsis seeds. The plate was sealed using a rubber sealing mat. The seeds were ground using a 2000 Geno/Grinder (Spex Certiprep, Inc (Metuchen, N.J.) for 10 minutes at 1500 strokes/minute.

Two sets of tubes were prepared for the extractions. The first set was labeled for the sample type and that the extraction contained proteinase K. The second set of tubes was labeled with the sample type and that no proteinase K was used in the extraction. In the first set of tubes 45 µl of Extraction Solution and 5 µl of Sample Preparation Solution, which contains Proteinase K was pipetted and mixed together. In the second set of tubes 50 µl of Extraction Solution was pipetted in. To each extraction tube 5 µl of the appropriate ground seed material was pipetted into the extraction mixture, and pipetted up and down to mix. Each mixture was incubated at 55° C. for 10 minutes to extract the DNA. Each extract was then incubated at 95° C. for 3 minutes to stop the extraction. To each stopped extraction 50 µl of Neutralization Solution B was pipetted in. The extractions were then vortexed to mix.

For standard PCR amplification, 10 µl of REDExtract-N-amp PCR™ mix (Sigma-Aldrich), both forward and reverse primers at 0.4 µM., and 4 µl of extract in a final volume of 20 µl. PCR Primers for Soybean were 513 bp, Sorghum, 503 bp, and Arabidopsis 2110 bp. Reactions were assembled at room temperature. PCR conditions for Soybean and Sorghum PCRs: 94° C. for 3 min, then 35 cycles of 94° C. for 30 sec, 44° C. for 30 sec, 68° C. for 45 sec, and 68° C. 7 min. For Arabidopsis PCR: 94° C. for 3 min, then 35 cycles of 94° C. for 30 sec, 49° C. for 30 sec, 68° C. for 2 min 15 sec, and 68° C. 7 min. 5 µl of PCR products were analyzed by gel electrophoresis on a 1% agarose gel in TBE.

Figure 2:
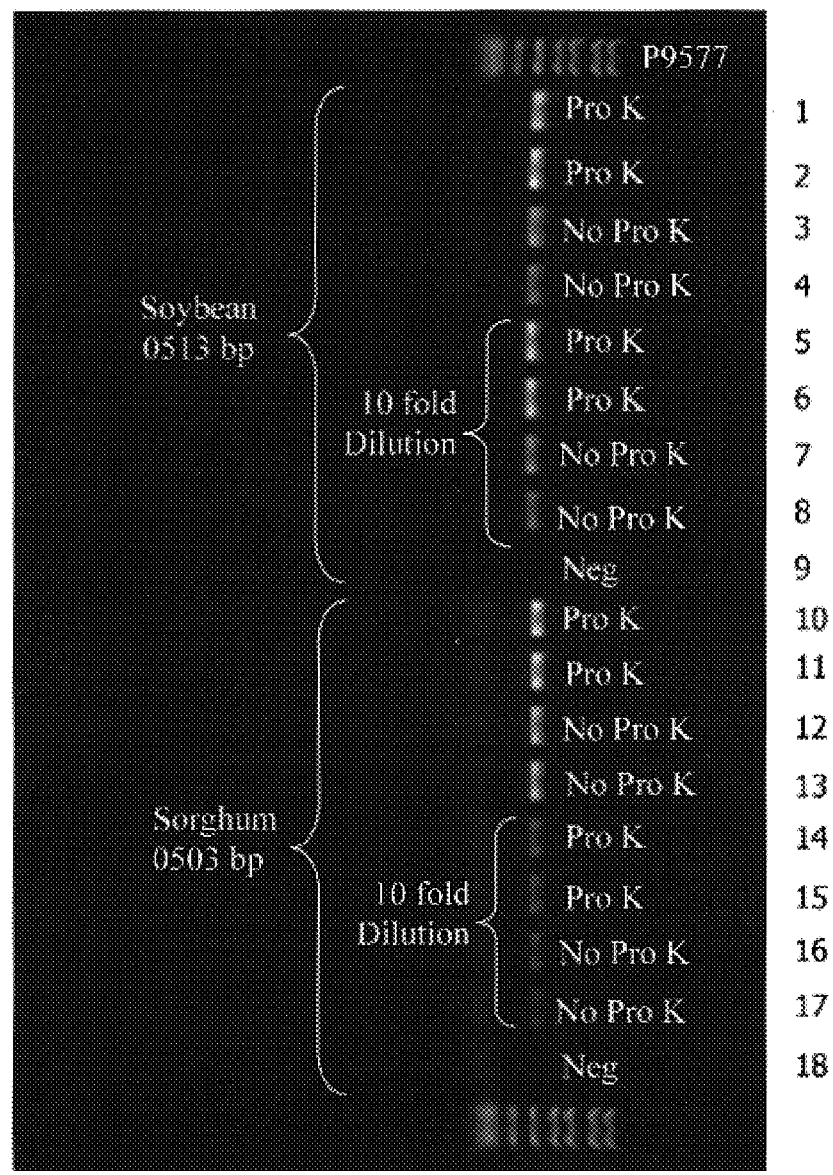
FIG. 2 illustrates in duplicate samples, agarose gel electrophoresis of PCR amplification products obtained from extraction of seeds from soybean as extracted (lanes 1–4) and as diluted by ten-fold (lanes 5–8) and from extraction of seeds from sorghum as extracted (lanes 10–13) and as diluted by ten-fold (lanes 14–17) in the presence (lanes 1, 2, 5, 6, 10, 11, 14, and 15) and absence of proteinase K (lanes 3, 4, 7, 8, 12, 13, 16, and 17).
Figure 3:
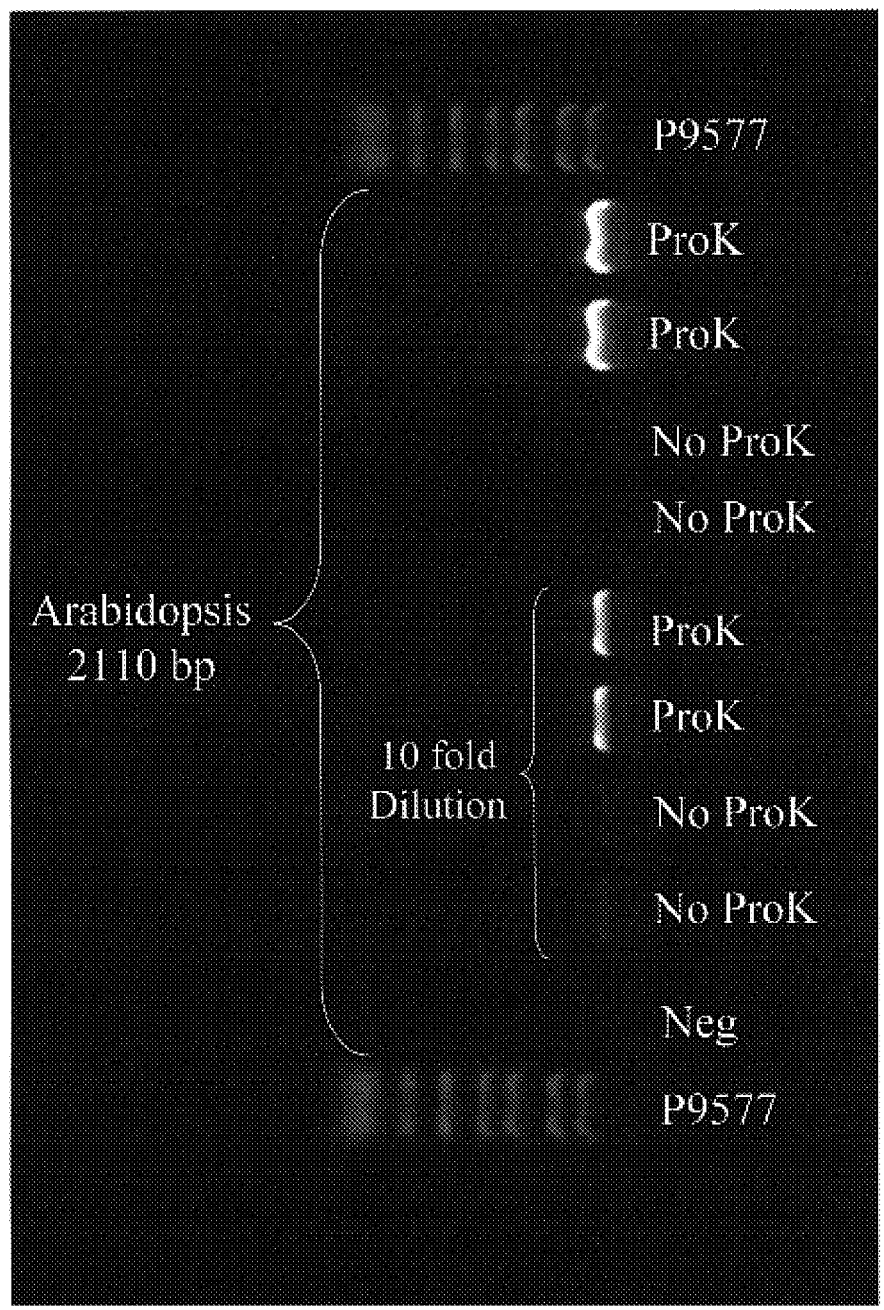
FIG. 3 illustrates in duplicate samples, agarose gel electrophoresis of PCR amplification products obtained from extraction of seeds from Arabidopsis as extracted (lanes 1–4) and as diluted by ten-fold (lanes 5–8) in the presence (lanes 1, 2, 5, and 6) and absence (lanes 3, 4, 7, and 8) of proteinase K.

As is seen in FIG. 2, proteinase K improves extraction of DNA from the seeds. The intensity of the bands from the soybean preps are brighter for the samples that included proteinase K in the extraction. This can be seen in both the PCR's on the neat extract and the PCR's on the 1:10 dilutions of the neat extract. There does not seem to be any effect on the sorghum preps whether or not proteinase K is included. A very large difference is seen in the PCR's of the Arabidopsis preps (FIG. 3). It is very apparent from FIG. 3 that the samples that did not have proteinase K in the extraction did not perform as well as those that had proteinase K in the extraction.

Thus, proteinase K improved extraction of DNA from soybean and Arabidopsis seeds, but it did not appear to improve extraction from the sorghum seeds tested.

EXAMPLE 5

This example compares the extraction efficiency of the method here and that reported earlier (Guidet, *Nucleic Acids Res.* 21:4153–4154, 1994).

Extractions were performed using seeds from soybean, sorghum, canola, wheat, and Arabidopsis. All materials were obtained from Sigma-Aldrich (St. Louis, Mo.) unless otherwise noted. All PCR primers were obtained from Sigma-Genosys (The Woodlands, Tex.). Primers used for Soybean, Sorghum and Arabidopsis were as described in Example 4. Primers used for Canola and Wheat were as follows:

```
Canola 0762 bp:  Forward-5'-CTT TTC CTC CCG CAC CTT-3'  (SEQ ID NO:9)
                 Reverse-5'-GCC GCC GAC TTG ATT TC-3'   (SEQ ID NO;10)

Wheat 0500 bp:   Forward-5'-AGT GGC GAG AGG AGG TTC-3'  (SEQ ID NO:11)
                 Reverse-5'-TGG TTG GCG ATT GTG G-3'    (SEQ ID NO:12)
```

Seeds were placed into wells of a 96 square well block. 1 seed was placed into 2 separate wells for Soybean, Sorghum, Canola, and Wheat. Around 50 Arabidopsis seeds were placed into 2 separate wells. A single Stainless Steel grinding ball was placed into each seed containing well. 800 µl of water is pipetted into the wells containing soybean seeds. 200 µl of water is pipetted into the wells containing sorghum, canola, and wheat seeds. 100 µl of water is pipetted into the wells containing arabidopsis seeds. The plate is sealed using a rubber sealing mat. The seeds are ground using a 2000 Geno/Grinder (Spex Certiprep, Inc (Metuchen, N.J.) for 10 minutes at 1500 strokes/minute.

For DNA extractions using the methods herein, two sets of tubes were prepared. The first set was labeled for the sample type and with method and the second set of tubes was labeled with the sample type, method and dilution for the 1:10 dilutions of the first set. In the first set of tubes 45 µl of Extraction Solution and 5 µl Sample Preparation Solution containing proteinase K were pipetted and mixed together. Into the second set of tubes 18 µl of a 50:50 mixture of Extraction Solution and Neutralization Solution B was pipetted. To each extraction tube 5 µl of the appropriate ground seed material was pipetted into the extraction mixture, and pipetted up and down to mix. Each mixture was incubated at 55° C. for 10 minutes to extract the DNA. Each extract was then incubated at 95° C. for 3 minutes to stop the extraction and denature the proteinase K. 50 µl of Neutralization Solution B was pipetted into each of the extraction mixtures. The extractions were then vortexed to mix. 2 µl of the neutralized extract was pipetted into the second set of tubes and vortexed to mix.

For DNA extractions using the method of Guidet (1994, supra) a solution was prepared containing 10 mM Tris-HCl, ph 8.0, 0.45 M EDTA, 1% lauryl sarkosyl, and 1 mg/ml Proteinase K as described in the paper. 100 µl of the Extraction Buffer were pipetted into a set of tubes labeled with the sample type and with a G to signify that they are the preparations of the method reported earlier. 5 µl of the ground seed material was pipetted into the correct tubes. The entire set of samples was then incubated at 50° C. for 1 hour. After the incubation the extracts were diluted with 150 µl of milliQ H$_2$O. 20 µl of the diluted extract was pipetted into tubes containing 80 µl of milliQ H$_2$O with 10 µg of RNase A. Samples were then incubated at 100° C. for 5 minutes. After the samples were allowed to cool to room temperature, 101 µl were pipetted into a new tube containing 240 µl of milliQ H$_2$O. The samples were vortexed to mix thoroughly.

PCR amplifications of extractions obtained using the methods herein, were performed using 10 µl of REDExtract-N-Amp PCR™ mix (Sigma-Aldrich, St. Louis, Mo.), both forward and reverse primers at 0.4 µM., and 4 µl of extract in a final volume of 20 µl. For the samples extracted using the method reported earlier by Guidet, the PCR was performed using 10 µl of REDExtract-N-Amp PCR™ mix (Sigma-Aldrich, St. Louis, Mo.), both forward and reverse primers at 0.4 µM, 4 µl of a 50:50 Extraction Solution and Neutralization Solution B mixture, and 5 µl of extract obtained using the method of Guidet, in a final volume of 20 µl. For the samples set up according to the method of Guidet, 1 unit of Jumpstart taq (Sigma-Aldrich, St. Louis, Mo.), 0.1 mM of each dNTP (Sigma-Aldrich, St. Louis, Mo.), 1× of Taq polymerase buffer (Sigma-Aldrich, St. Louis, Mo.), 0.4 µM of each primer and 5 µl of extract obtained using the method of Guidet in a final volume of 20 µl. PCR Primers for Soybean were 513 bp, sorghum, 503 bp, canola 762 bp, wheat 500 bp and Arabidopsis 2110 bp. Reactions were assembled at room temperature. PCR conditions for soybean and sorghum PCRs: 94° C. for 3 min, then 35 cycles of 94° C. for 30 sec, 44° C. for 30 see, 68° C. for 45 sec, and 68° C. 7 min. For canola and wheat PCRs: 94° C. for 3 min, then 35 cycles of 94° C. for 30 sec, 55° C. for 30 sec, 68° C. for 1 min, and 68° C. 7 min. For Arabidopsis PCR: 94° C. for 3 min, then 35 cycles of 94° C. for 30 sec, 49° C. for 30 sec, 68° C. for 2 min 15 sec, and 68° C. 7 min. 5 µl of all red PCR product and 6 µl of the clear product, with 4 µl of loading buffer (G2526) added to the entire PCR volume, were analyzed by gel electrophoresis on a 1% agarose gel in TBE. The gel was run at 125 V for 1 hour.

Figure 4:
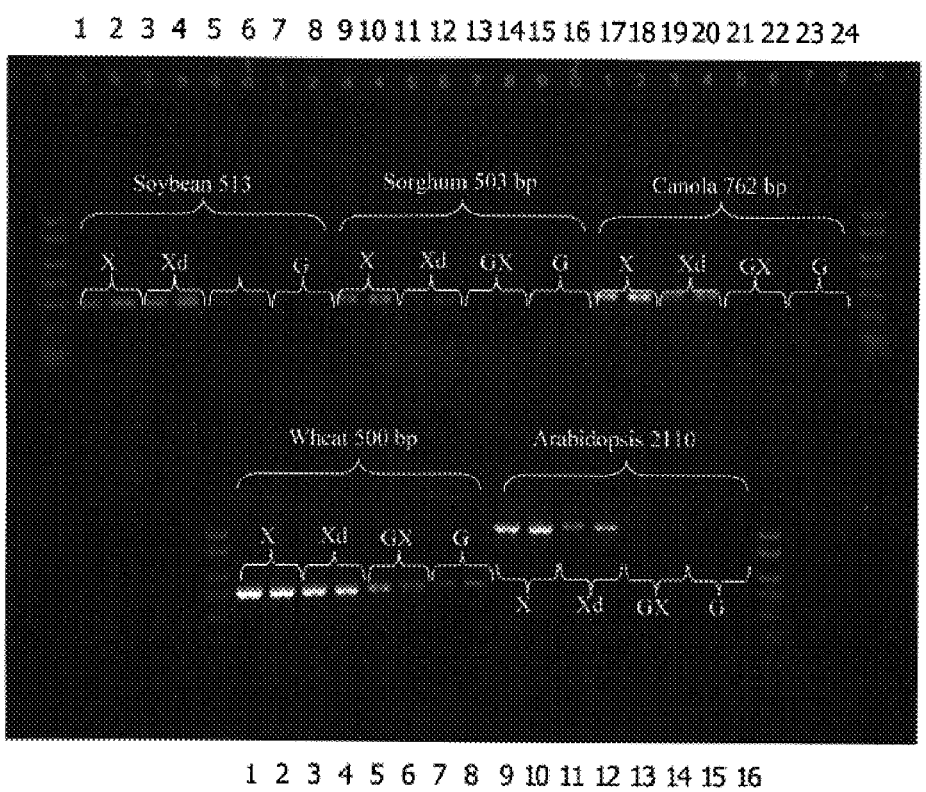
FIG. 4 illustrates in duplicate samples, agarose gel electrophoresis of PCR amplification products obtained from extraction of seeds from soybean, sorghum, canola, wheat, and arabidopsis as extracted (Row I, lanes 1, 2, 5, 6, 7, 8, 9, 10, 13, 14, 15, 16, 17, 18, 21, 22, 23, and 24; Row II, lanes 1, 2, 5, 6, 7, 8, 9, 10, 13, 14, 15, and 16) and as diluted by ten-fold (Row I, lanes 3, 4, 11, 12, 19 and 20; Row II, lanes 3, 4, 11, and 12) using the extraction method herein (Row I, lanes 1–4, 9–12 and 17–20; Row II, lanes 1–4 and 9–12) the extraction method described by Guidet (Guidet, *Nucleic Acids Res.* 21:4153–4154, 1994) with the PCR mix from the method herein (Row I, lanes 5, 6, 13, 14, 21, and 22; Row II, lanes 5, 6, 13, and 14) and the extraction method described by Guidet with the PCR setup as described by Guidet (Row I, lanes 7, 8, 15, 16, 23, and 24; Row II, lanes 7, 8, 15, and 16)

As seen in FIG. 4, the extraction method herein produced substantially more PCR amplification product from all the seeds tested than was the method reported by Guidet. Furthermore, the decreased time of 10 minutes required for the method herein was a substantial shortening of the one hour extraction time required by the earlier method of Guidet.

EXAMPLE 6

This example illustrates the effects of varying the different components of the Extraction Solution and Sample Preparation Solution on effectiveness of extraction.

Frozen mouse tails were used to test the individual components of the extraction composition, which was made up of the Extraction Solution and Sample Preparation Solution. A factorial experimental design evaluated all possible combinations of the components the extraction composition. Table 1 below shows the combinations tested.

TABLE 1

| Test No. | KCl | EDTA | Tris-HCl | Pro K |
|---|---|---|---|---|
| 1 | 0 | 0 | 0 | 0 |
| 2 | 0 | 10 mM | 0 | 0 |
| 3 | 0 | 0 | 100 mM | 0 |
| 4 | 0 | 10 mM | 100 mM | 0 |
| 5 | 0 | 0 | 0 | 4 ug/ml |
| 6 | 0 | 10 mM | 0 | 4 ug/ml |
| 7 | 0 | 0 | 100 mM | 4 ug/ml |
| 8 | 0 | 10 mm | 100 mM | 4 ug/ml |
| 9 | 250 mM | 0 | 0 | 0 |
| 10 | 250 mM | 10 mM | 0 | 0 |

TABLE 1-continued

| Test No. | KCl | EDTA | Tris-HCl | Pro K |
|---|---|---|---|---|
| 11 | 250 mM | 0 | 100 mM | 0 |
| 12 | 250 mM | 10 mM | 100 mM | 0 |
| 13 | 250 mM | 0 | 0 | 4 ug/ml |
| 14 | 250 mM | 10 mM | 0 | 4 ug/ml |
| 15 | 250 mM | 0 | 100 mM | 4 ug/ml |
| 16 | 250 mM | 10 mM | 100 mM | 4 ug/ml |

All materials were obtained from Sigma-Aldrich (St. Louis, Mo.) unless otherwise noted. All PCR primers were obtained from SigmaGenosys (The Woodlands, Tex.). All reagents were obtained from Sigma-Aldrich (St. Louis, Mo.).

DNA extractions were performed as follows. Mouse tail snips (0.5 cm tail tip) were collected earlier and kept frozen at −20° C. for up to several months before use. Each extraction was setup by placing 1 mouse tail into a 1.5 ml microcentrifuge tube. The method used was as described in Example 1.

One tube was prepared for the extraction of each condition. In each tube 100 μl of each extraction mixture and 25 μl Sample Preparation Solution or water was pipetted and mixed together in each tube, which already contained a mouse tail. Each mixture was incubated at room temperature, i.e. approximately 22° C. for 10 minutes to extract the DNA. Each extraction was then incubated for 3 minutes at 95° C. To each extraction mixture, 100 μl of Neutralization Solution B was added. The extractions were then vortexed to ensure thorough mixing of reagents. The extracts were then ready for PCR amplification.

For standard PCR in 8 tube strips, 10 μl of REDExtract-N-amp PCR™ Ready mix (Sigma-Aldrich, St. Louis, Mo.), both forward and reverse primers at 0.4 μM., and 4 μl of extract, in a final volume of 20 μl. Two master mixes were prepared because half of the extracts did not contain KCl, which is essential for the proper performance of the kit PCR mixes, so extra KCl was added to one mix and not the other. PCR Primers for mouse tails produced an 1181 bp amplicon from the Mouse Interleukin One Beta (IL-1β) gene. The primers were as follows: forward primer: 5'-TCTGGGGT-TGATGTAGGA-3' SEQ ID NO:13) and reverse primer: 5'-GGGCTGGAAAAATGGTC-3'). (SEQ ID NO:14) Reactions were assembled at room temperature and placed in a GeneAmp PCR System 9700 (Perkin Elmer/Applied Biosystems, Foster City, Calif.). PCR conditions for mouse tail reactions: 94° C. for 3 min, then 35 cycles of 94° C. for 45 sec, 58° C. for 60 sec, 72° C. for 120 sec, then 72° C. 7 min. The completed reactions were analyzed by gel electrophoresis (5 μl/PCR reaction) on a 1×TBE 2% Seakem LE Plus 10×15 Latitude Precast agarose gel with 0.5 μg/ml Ethidium Bromide added from BioWhittaker Molecular Applications (Rockland, Me.) (Cat. No. 57231-lot No. LT0902). The gel was run in 0.5×TBE running buffer, which is a dilution of Tris-Borate-EDTA Buffer 5× Concentrate (T6400). Using a submarine gel electrophoresis rig (E1138) run at 125 volts for 45 minutes. The marker used on the gel was P9577 PCR Marker (bands of 2000, 1500, 1000, 750, 500, 300, 150 & 50 bp).

DNA positive controls were prepared from 1.2 cm of mouse tail with GenElute™ Mammalian Genomic DNA Kit (Sigma-Aldrich, St. Louis, Mo.). The purified DNA was diluted to 57.5 ng/μl, and 2-fold serial dilutions were prepared from the 57.5 ng/μl dilution until a dilution ~12.5 ng/μl was reached, then 1 μl is used in the positive control for the PCR mixes. Negative controls consist of 4 μl of a 50/50 mixture of Extraction Solution and Neutralization Solution B in the PCR reaction.

Figure 5:
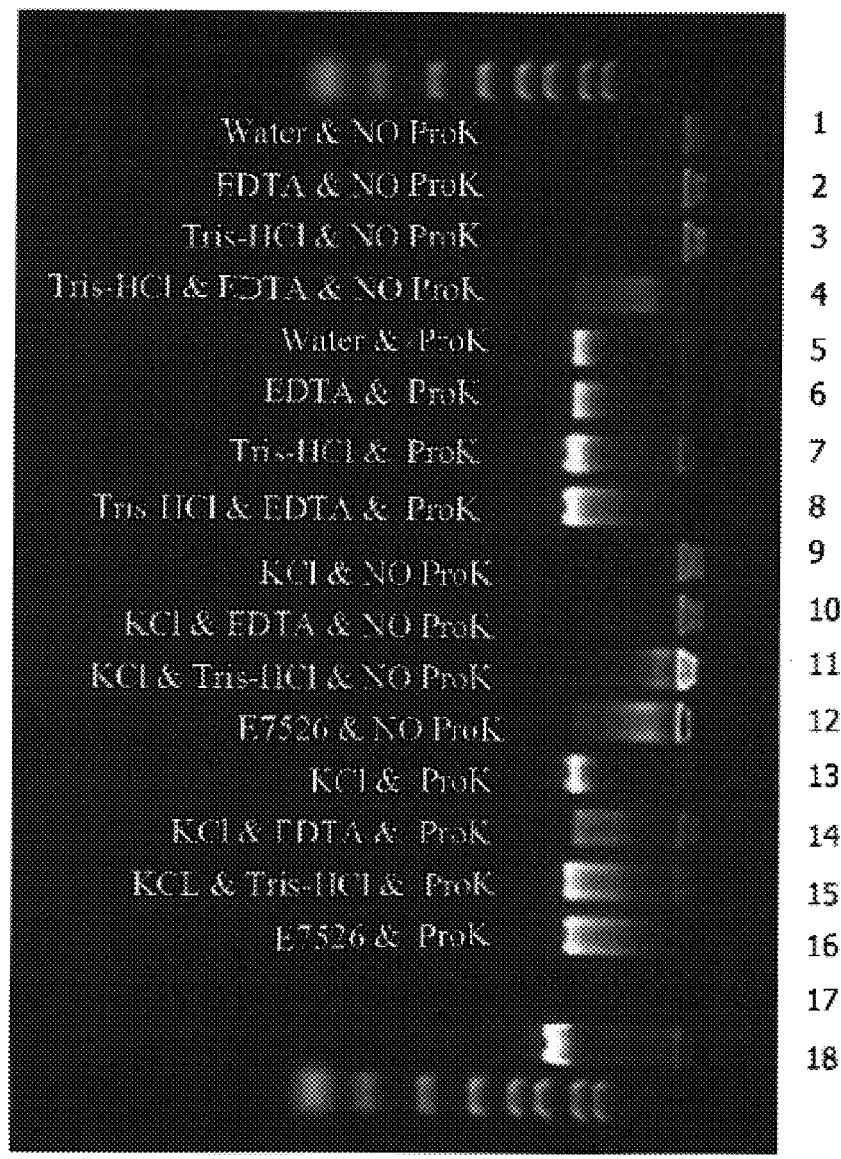
FIG. 5 illustrates in single samples, agarose gel electrophoresis of PCR amplification products obtained from extraction of mouse tails in which various components were absent or present showing the effect of absence (lanes 1–4 and 9–12) and presence (lanes 5–8 and 13–16) of proteinase K, the effects of water (lanes 1 and 5), EDTA (lanes 2 and 6), Tris-HCl (lanes 3 and 7), Tris-HCl and EDTA (lanes 4 and 8), KCl (lanes 9 and 13), KCl and EDTA (lanes 10 and 14), KCl and Tris-HCl (lanes 11 and 15), and Extraction Solution (E7526)(lanes 12 and 16).

As seen in FIG. 5, the presence of proteinase K and the Tris-HCl buffer improve extraction efficiency. Extraction Solution, E7526 was as identified in Example 1.

The study was repeated to confirm the results using duplicate samples. Table 2 below shows all combinations tested in the follow-up study.

TABLE 2

| Test No. | KCl | EDTA | Tris-HCl | Pro K |
|---|---|---|---|---|
| 1 | 0 | 0 | 100 mM | 4 ug/ml |
| 2 | 0 | 10 mm | 100 mM | 4 ug/ml |
| 3 | 250 mM | 0 | 100 mM | 4 ug/ml |
| 4 | 250 mM | 10 mM | 100 mM | 4 ug/ml |

Materials and methods were as described above.

Figure 6:
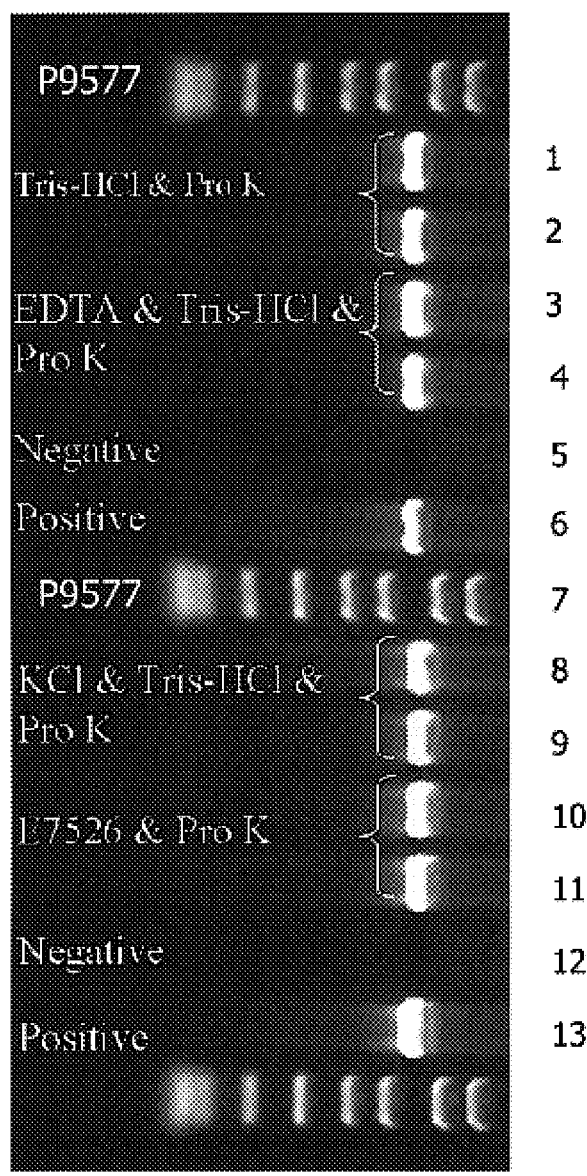
FIG. 6 illustrates in duplicate samples, agarose gel electrophoresis of PCR amplification products obtained from extraction of mouse tails in which various components were absent or present showing the effect of Tris-HCl and proteinase K (lanes 1 and 2); EDTA, Tris-HCl and proteinase K (lanes 3 and 4), KCl, Tris-HCl and proteinase K (lanes 8 and 9) and Extraction Solution (lanes 10 and 11) with lanes 5 and 12 and lanes 6 and 13 showing negative and positive controls, respectively.

As seen in FIG. 6, the E7526 Extraction Solution as identified in Example 1, worked well if not better than the other 3 combinations of components in the factorial study. The Tris-HCl component and proteinase K component were present in all samples and all showed excellent extraction. Taken together with the first factorial study, the buffering component, Tris-HCl and proteinase K are believed to be the most important factors. The proteinase K works well when a constant pH is maintained.

The duplicate samples in the second part of the study help show consistency of the results for each set of conditions. The E7526 Extraction Solution with proteinase K was slightly brighter than the other combination (FIG. 6). The KCl seems to make little difference in the extractions, although its presence is needed for the subsequent PCR mix.

As various changes could be made in the above methods and compositions without departing from the scope of the invention, it is intended that all matter contained in the above description be interpreted as illustrative and not in a limiting sense.

All references cited in this specification are hereby incorporated by reference. The discussion of the references herein is intended merely to summarize the assertions made by their authors and no admission is made that any reference constitutes prior art relevant to patentability. Applicant reserves the right to challenge the accuracy and pertinency of the cited references.

What is claimed is:

1. A kit for extracting nucleic acids from tissue samples for polymerase chain reaction (PCR) amplification, wherein the tissue sample is incubated in an extraction composition for not more than 60 minutes, the kit comprising components of a nucleic acid extraction composition, packaged separately or in one or more mixtures of any combination thereof, each separate component or mixture being in a different container for mixing prior to use, the components of the extraction composition comprising a protease enzyme, a buffering component which maintains the pH at 7.5 or greater in the extraction composition and a $Ca^{2+}$-chelator which produces a concentration of not more than about 100 mM of said $Ca^{2+}$-chelator in the extraction composition upon mixing the components, wherein the components of the extraction composition do not include a surface active agent.

2. A kit in accordance with claim 1, wherein the kit comprises an extraction solution which contains the buffering component and the $Ca^{2+}$-chelator and a sample preparation solution which contains the protease enzyme.

3. A kit in accordance with claim 1, wherein the protease enzyme is a subtilisin-like serine protease.

4. A kit in accordance with claim 3, wherein the subtilisin-like serine protease is proteinase K.

5. A kit in accordance with claim 4, wherein the proteinase K is present at a concentration of about 50 Units/ml or greater.

6. A kit in accordance with claim 5, wherein the proteinase K is present at a concentration of about 100 Units/ml or greater.

7. A kit in accordance with claim 1, wherein the $Ca^{2+}$-chelator is ethylenediaminetetraacetic acid (EDTA) in a sufficient amount to yield not more than about 100 mM EDTA in the extraction composition.

8. A kit in accordance with claim 6, wherein the EDTA is in a sufficient amount to yield not more than about 10 mM EDTA.

9. A kit in accordance with claim 1, wherein the buffering component comprises Tris-HCl buffer.

10. A kit in accordance with claim 1, wherein the Tris-HCl buffer component yields a concentration of about 80 mM or greater in the extraction composition.

11. A kit in accordance with claim 1, wherein the extraction composition is buffered to a pH of at least 8.0 or greater.

* * * * *